United States Patent
Kou

(10) Patent No.: US 7,820,199 B2
(45) Date of Patent: *Oct. 26, 2010

(54) STABLE EXTENDED RELEASE ORAL DOSAGE COMPOSITION

(75) Inventor: Jim H. Kou, Basking Ridge, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/244,743

(22) Filed: Oct. 6, 2005

(65) Prior Publication Data

US 2006/0159761 A1 Jul. 20, 2006

Related U.S. Application Data

(63) Continuation of application No. 10/175,460, filed on Jun. 19, 2002, now Pat. No. 6,979,463, which is a continuation-in-part of application No. PCT/US00/34412, filed on Dec. 19, 2000.

(60) Provisional application No. 60/172,836, filed on Dec. 20, 1999.

(51) Int. Cl.
*A61K 9/20* (2006.01)
*A61K 9/28* (2006.01)

(52) U.S. Cl. .................. 424/468; 424/474; 424/480

(58) Field of Classification Search .................. None
See application file for complete search history.

(56) References Cited

U.S. PATENT DOCUMENTS

| | | | |
|---|---|---|---|
| 3,536,809 A | 10/1970 | Applezweig | 424/28 |
| 3,598,123 A | 8/1971 | Zaffaroni | 128/268 |
| 3,845,770 A | 11/1974 | Theeuwes et al. | 128/260 |
| 3,916,899 A | 11/1975 | Theeuwes et al. | 128/260 |

(Continued)

FOREIGN PATENT DOCUMENTS

EP 0 264 259 A1 4/1988

(Continued)

OTHER PUBLICATIONS

Cardelus et al., "Anticholinergic effects of desloratadine, the major metabolite of loratadine, in rabbit and guinea-pig iris smooth muscle", European Journal of Pharmacology, 374:249-254, 1999.

(Continued)

*Primary Examiner*—Robert A Wax
*Assistant Examiner*—Melissa S Mercier
(74) *Attorney, Agent, or Firm*—Barry H. Jacobsen

(57) ABSTRACT

A film-coated extended release solid oral dosage composition containing a nasal decongestant, pseudoephedrine or salt thereof, e.g., pseudoephedrine sulfate in a core effective to provide a geometric maximum plasma concentration of pseudoephedrine of about 345 ng/mL to about 365 ng/mL at a time of about 7.60 hrs to about 8.40 hrs and having two or three film-coatings on the core, the second one containing an amount of the non-sedating antihistamine, desloratadine, effective to provide a geometric maximum plasma concentration of desloratadine of about 2.15 ng/mL to about 2.45 ng/mL at a time of about 4.0 hours to about 4.5 hours, and use of the composition for treating patients showing the signs and symptoms associated with allergic and/or inflammatory conditions of the skin and airway passages are disclosed.

16 Claims, 1 Drawing Sheet

CHART

U.S. PATENT DOCUMENTS

| | | | |
|---|---|---|---|
| 3,940,485 A | 2/1976 | Levinson et al. | 424/250 |
| 4,008,796 A | 2/1977 | Aylon | 198/460 |
| 4,282,233 A | 8/1981 | Vilani | 424/267 |
| 4,371,516 A | 2/1983 | Gregory et al. | 424/22 |
| 4,552,899 A | 11/1985 | Sunshine et al. | 514/568 |
| 4,659,716 A | 4/1987 | Villani et al. | 514/290 |
| 4,731,447 A | 3/1988 | Schumacher et al. | 546/93 |
| 4,777,170 A | 10/1988 | Heinrich | 514/226.2 |
| 4,783,465 A | 11/1988 | Sunshine et al. | 514/255 |
| 4,804,666 A | 2/1989 | Piwinski et al. | 514/278 |
| 4,863,931 A | 9/1989 | Schumacher et al. | 514/290 |
| 4,906,647 A | 3/1990 | Kouchiwa et al. | 514/356 |
| 4,917,900 A * | 4/1990 | Jones et al. | 424/493 |
| 4,990,535 A | 2/1991 | Cho et al. | 514/556 |
| 5,019,591 A | 5/1991 | Gardner et al. | 514/461 |
| 5,089,496 A | 2/1992 | Piwinski et al. | 514/253 |
| 5,100,675 A | 3/1992 | Cho et al. | |
| 5,314,697 A * | 5/1994 | Kwan et al. | 424/480 |
| 5,407,941 A | 4/1995 | Carceller et al. | 514/290 |
| 5,476,856 A | 12/1995 | Carceller et al. | 514/290 |
| 5,487,901 A | 1/1996 | Conte et al. | |
| 5,508,042 A | 4/1996 | Oshlack et al. | |
| 5,595,997 A | 1/1997 | Aberg et al. | 514/290 |
| 5,731,319 A * | 3/1998 | Aberg et al. | 514/290 |
| 5,807,579 A | 9/1998 | Vilkov et al. | 424/469 |
| 5,900,421 A | 5/1999 | Handley et al. | 514/290 |
| 5,939,426 A | 8/1999 | McCullough | 514/290 |
| 5,962,464 A | 10/1999 | Handley et al. | |
| 5,997,903 A | 12/1999 | Dietrich et al. | |
| 6,051,585 A | 4/2000 | Weinstein et al. | 514/335 |
| 6,100,274 A | 8/2000 | Kou | 514/290 |
| 6,114,346 A | 9/2000 | Harris | |
| 6,132,758 A | 10/2000 | Munayyer et al. | 424/439 |
| 6,270,796 B1 | 8/2001 | Weinstein et al. | 424/457 |
| 6,372,802 B2 | 4/2002 | Hellberg et al. | |
| 6,423,721 B1 | 7/2002 | Harris et al. | |
| 6,432,972 B2 | 8/2002 | Salmun et al. | |
| 6,506,767 B1 | 1/2003 | Schumacher et al. | 514/290 |
| 6,514,520 B2 | 2/2003 | Munayyer et al. | 424/439 |
| 6,521,254 B2 | 2/2003 | Weinstein et al. | 424/468 |
| 6,599,913 B1 | 7/2003 | Johnson et al. | |
| 6,709,676 B2 | 3/2004 | Cho | |
| 7,405,223 B2 | 7/2008 | Affrime et al. | |
| 7,618,649 B2 | 11/2009 | Cho | |
| 2004/0097536 A1 | 5/2004 | Cho | |

FOREIGN PATENT DOCUMENTS

| | | |
|---|---|---|
| EP | 0 288640 A1 | 11/1988 |
| EP | 0173928 B1 | 6/1990 |
| EP | 0 396404 A1 | 11/1990 |
| EP | 0 577 957 A1 | 1/1994 |
| EP | 0 396404 B1 | 2/1994 |
| EP | 0655744 B1 | 1/2000 |
| EP | 1112738 A2 | 7/2001 |
| WO | WO 85/03707 | 8/1985 |
| WO | WO 92/00293 | 1/1992 |
| WO | WO 92/11034 | 7/1992 |
| WO | WO 92/20377 | 11/1992 |
| WO | WO-94/09761 A1 | 5/1994 |
| WO | WO 96/16641 | 6/1996 |
| WO | WO 96/20708 | 7/1996 |
| WO | WO 98/34614 | 8/1998 |
| WO | WO 00/02560 | 1/2000 |

OTHER PUBLICATIONS

Kosoglou et al., "Pharmacokinetics of Loratadine and Pseudoephedrine Following Single and Multiple Doses of Once- Versus Twice-Daily Combination Tablet Formulations in Healthy Adult Males" Clinical Therapeutics, 19(5):1002-1012, 1997.

Kreutner et al., "Preclinical Pharmacology of Desloratadine, a Selective and Nonsedating Histamine H1, Receptor Antagonist. 2nd Communication: Lack of central nervous system and cardiovascular effects" Arzneimittel-Forschung/Drug Res., 50(5):441-448, 2000.

Nomeir et al., "Influence of Food on the Oral Bioavailability of Loratadine and Pseudoephedrine from Extended-Release Tablets in Healthy Volunteers" J. Clin Pharmacology, 36:923-930, 1996.

Connors, et al., Chemical Stability of Pharmaceuticals, a Handbook for Pharmacists, 135-159 (John Wiley & Sons 1986).

Technology of Drug Forms, Educational Literature for Students of Pharmaceutical Institutes, vol. 2, 134, 187, 188, 189 (L.A. Ivanova, ed.) (Moscow, "Meditsina" 1991).

Food and Drug Administration / Center for Drug Evaluation and Research, Guidance for Industry—Q3B Impurities in New Drug Products (Nov. 1997).

Food and Drug Administration / Center for Drug Evaluation and Research, Guidance for Industry—Dissolution Testing of Immediate Release Solid Oral Dosage Forms (Aug. 1997).

Food and Drug Administration / Center for Drug Evaluation and Research, Guidance for Industry—SUPAC-MR: Modified Release Solid Oral Dosage Forms, Scale-Up and Postapproval Changes: Chemistry, Manufacturing, and Controls; In Vitro Dissolution Testing and In Vivo Bioequivalence Documentation (Sep. 1997).

International Conference on Harmonisation of Technical Requirements for Registration of Pharmaceuticals for Human Use, ICH Harmonised Tripartite Guideline—Impurities in New Drug Products Q3B(R2), Current Step 4 Version (Jun. 2, 2006).

USP 30 / NF 25, vol. 1, 277-284 (2007).

Andersen, et al., "Adverse drug interactions clinically important for the dermatologist", Arch Dermatol, Apr. 1995, vol. 131, pp. 468-473.

Babe, et al., "Histamine, Bradykinin, and their Antagonists" in The Pharmacological Basis of Therapeutics ($9^{th}$ edition), The McGraw-Hill Co. Inc., pp. 581-599 (1996).

Barnett, et al., "Pharmacology of Non-Sedating H1 Antihistamines" *New Perspectives in Histamine Research*, Birkhauser Verlag Basel, pp. 181-196 (1991).

Berge, et al., "Pharmaceutical Salts", J. of Pharm. Sciences, Jan. 1977, vol. 66, No. 1, pp. 1-19.

Berthon, et al., "In Vitro inhibition, by loratadine and descarboxyethoxyloratadine, of histamine release from human basophils, and of histamine release and intracellular calcium fluxes in rat basophilic leukemia cells (RBL-2H3)", Biochem. Pharm., 1994, vol. 47, No. 5, pp. 789-794.

Blaug, et al., "Interaction of dextroamphetamine sulfate with spray-dried lactose", J. of Pharm. Sciences, Nov. 1972, vol. 61, No. 11, pp. 1770-1775.

Brandes, et al., "Enhanced cancer growth in mice administered daily human-equivalent doses of some H1-antihistamines: predictive in vitro correlates", J. of the National Cancer Inst., May 18, 1994, vol. 86, No. 10, pp. 770-775.

Brandes, et al., "Stimulation of malignant growth in rodents by antidepressant drugs at clinically relevant doses", Cancer Research, Jul. 1, 1992, vol. 52, pp. 3796-3800.

Brion, et al., "Evaluation of the antimuscarinic activity of atropine, terfenadine and mequitazine in healthy volunteers", Br. J. Clin. Pharmac. 1988, vol. 25, pp. 27-32.

Carmeliet, "Voltage- and Time-Dependent Block of the Delayed K+ Current in Cardiac Myocytes by Dofetilide", The J. of Pharm. And Experimental Therapeutics, 1992, vol. 262, No. 2, pp. 809-817.

Castello, et al., "Discoloration of tablets containing amines and lactose", J. of Pharm. Sciences, Feb. 1962, vol. 51, No. 2, pp. 106-108.

Cheung, et al., "Investigation of anti-motion sickness drugs in the squirrel monkey", J. Clin. Pharmacol, 1992, vol. No. 32, pp. 163-175.

Clissold, et al., "Loratadine: A preliminary review of its pharmacodynamic properties and therapeutic efficacy", Drugs, 1989, vol. 37, pp. 42-57.

Cooke, "Glycopyrrolate in bladder dysfunction", SA Medical Journal, Jan. 1, 1983, p. 3.

Craft, "Torsade de pointes after astemizole overdose", Br. Medical Journal, 1986, vol. 292, p. 660.

Dorje, et al., "Antagonist Binding Profiles of Five Cloned Human Muscarinic Receptor Subtypes", The J. of Pharm. And Experimental Therapeutics, 1991, vol. 256, pp. 727-733.

Drug Facts and Comparisons, 1998 Ed., Facts and Comparisons, St. Louis, Missouri, p. 2832.

Ebert, "Soft elastic gelatin capsules: a unique dosage form", Pharmaceutical Technology, 1977, pp. 44-50.

Gengo, "Dilemma: Antihistamine Selection: Use vs. Side Effects", U.S. Pharmacist, Nov. 1990, vol. 15, No. 22, pp. 59-60,62,24,68,70 & 72.

Hartauer, et al., A Comparison of Diffuse Reflectance FT-IR Spectroscopy and DSC in the Characterization of a Drug-Excipient Interaction, "Drug Development and industrial Pharmacy", 1991, vol. 17, No. 4, pp. 617-630.

Herron, et al, "Dose Proportionality, Linearity, and Pharmacokiinetics of Desloratadine in Healthy Volunteers" (Abstract 1126), J. Allergy Clin. Immunol., Jan. 2000, vol. 105, No. 1, Part 2, p. S385.

Herzog, et al., "Urinary Incontinence: medical and Psychosocial Aspects", *Annual Review of Gerontology and Geriatrics*, 1989, vol. 9, pp. 74-119.

Hilbert, et al., "Pharmacokinetics and Dose Proportionality of Loratadine", J. Clin. Pharmacol. 1987, vol. 27, pp. 694-698.

Housley, et al., "Histamine and related substances influence neurotransmission in the semicircular canal", Hearing Research, May 1, 1988, vol. 35, pp. 87-97.

Jankowski, et al., "Effect of Terfenadine on Nnasal Provocation", Int. Arch. Allergy Immunolog., 1993, vol. 101, pp. 311-317.

Kaliner, "Nonsedating Antihistamines: Pharmacology, Clinical Efficacy and Adverse Effects", American Family Physician, Mar. 1992, vol. 45, No. 3, pp. 1337-1342.

Kleine-Tebbe, et al., "Inhibition of IgE- and non-IgE-mediated histamine release from human basophil leukocytes in vitro by a histamine H1-antagonist, desethoxycarbonyl-loratadine", J. Allergy Clin. Immunol., 1994, vol. 93, pp. 494-500.

Knowles, "Astemizole and Terfenadine-Induced Cardiovascular Effects", The Canadian J. of Hospital Pharmacy, Feb. 1992, vol. 45, No. 1, pp. 33 & 37.

Kohl, et al., "Lack of Effects of Astemizole on Vestibular Ocular Reflex, Motion Sickness, and Cognitive Performance in Man", Aviation, Space, and Environmental Medicine, Dec. 1987, pp. 1171-1174.

Kohl, et al., "New Pharmacologic Approaches to the Prevention of Space/Motion Sickness", J. Clin. Pharmacol., 1991, vol. 31, pp. 934-946.

Kohl., et al., "Control of Nausea and autonomic dysfunction with terfenadine, a peripherally acting antihistamine", Aviation, Space and Environmental Medicine, May 1991, pp. 392-396.

Kreutner, et al, "Profile of Desloratadine as a Selective and Non-Sedating Histamine H1-Receptor Antagonist", Preclinical Efficacy and Antiallergic, J. Allergy Clin. lmmunol. (Abstract 1118), vol. 105, No. 1, part 2, pp. S382-383, Mar. 2000.

Kubo, et al., "Antimuscarinic Effects of Antihistamines: Quantitative Evaluation by Receptor-Binding Assay", Japan J. Pharmacol., 1987, vol. 43, pp. 277-282.

Lathers, et al., "Pharmacology in space: Part 2. Controlling motion sickness", TiPS, Jun. 1989, vol. 10, pp. 243-250.

Levin, et al., "Direct Measurement of the Anticholinergic Activity of a Series of Pharmacological Compounds on the Canine and Rabbit Urinary Bladder", The J. of Urology, Aug. 1982, vol. 128. pp. 396-398.

Lunde, "Antihistamines", *Side Effects of Drugs Annual 14*, Elsevier Science Publishers B.V., 1990, pp. 135-138.

Lunde, "Antihistamines", *Side Effects of Drugs Annual 12; A Worldwide Yearly Survey of New Data and Trends*, Elsevier Science Publishers B.V., 1998, pp. 142-143.

Massad, et al., "The Pharmacokinetics of Intravesical and Oral Oxybutynin Chloride", The J. of Urology, Aug. 1992, vol. 148, pp. 595-597.

McCue, "Safety of Antihistamines in the Treatment of Allergic Rhinitis in Elderly Patients", Arch. Fam. Med., Sep. 1996, vol. 5, pp. 464-468.

Miadonna, et al., "Inhibitory Effect of the H1 Antagonist Loratadine on Histamine Release From Human Basophils", Int. Arch. Allergy Immunol., 1994, vol. 105, pp. 12-17.

Mirakhur, et al., "Glycopyrrolate: Pharmacology and Clinical Use", Anaesthesia, 1983, vol. 38, pp. 1195-1203.

Mitchelson, "Pharmacological Agents Affecting Emesis: A Review (Part II)", Drugs, 1992, vol. 43, No. 4, pp. 443-463.

Muskat, et al., "The Use of Scopolamine in the Treatment of Detrusor Instability", The J. of Urology, 1996, vol. 156, pp. 1989-1990.

Nelemans, "Antiallergic and antitussive drugs", *Side Effects of Drugs Annual 12*, Elsevier Science Publishers B.V., 1988, pp. 144-147.

Nomeir, et al., "Influence of Food on the Oral Bioavailability of Loratadine and Pseudoephedrine from Extended-Release Tablets in Healthy Volunteers", J. Clin. Pharm, 1996, vol. 36, No. 10, pp. 923-930.

Padhi, et al., Multiple-Dose Pharmacokinetics; Safety and Tolerance of Desloratadine in Healthy Volunteers (Abstract 1124), Jan. 2000, J. Allergy Clin. Immunol., Jan. 2000, vol. 105, No. 1, part 2, p. S385.

Parkinson, et al., "Evaluation of Loratadine as an Inducer of Liver Microsomal Cytochrome P450 in Rats and Mice", Biochemical Pharmacology, 1992, vol. 43, No. 10, pp. 2169-2180.

Peggs, et al., "Antihistamines: The Old and the New", American Family Physician, Aug. 1995,vol. 52, No. 2 , pp. 593-600.

Petrin, "Bewegungskrankheit und ihre Therapie/ Eine Ubersicht (Motion Sickness and its Treatment)", Schweiz, Rundschau Med., 1974, (PRAXIS) 63, pp. 79-81.

Quercia, et al., "Focus on Loratadine: A new second-generation nonsedating H1-receptor antagonist", Hosp. Formul., Feb. 1993, vol. 28, pp. 137, 138, 141, 142, 144, 149, & 153.

Remington's Pharmaceutical Sciences. 18th Ed, Alfonso R. Gennaro, Mack Publishing Company, Easton, PA, 1990, pp. 1519-1520.

Remington's Pharmaceutical Sciences. 18th Ed, Alfonso R. Gennaro, Mack Publishing Company, Easton, PA, 1990, pp. 1527-1529.

Resnick, "Urinary incontinence", The Lancet, Jul. 8, 1995, vol. 346, pp. 94-99.

Roman, et al., "Loratadine-A Review of Recent Finding in Pharmacology Pharmacokinetics, Efficacy, and Safety, with a Look at its Use in Combination with Pseudoephedrine", Clin. Reviews in Allergy, 1993, vol. 11, pp. 89-110.

Salmun, et al., Efficacy and Safety of Desloratadine in Seasonal Allergic Rhinitis, Jan. 2000, J. Allergy Clin. Immunol. (Abstract 1123), vol. 105, No. 1, Part 2, pp. S384-385.

Simons, "H1-Receptor Antagonists Comparative Tolerability and Safety", Drug Safety, 1994, vol. 10, No. 5, pp. 350-380.

Sunahara, et al., "Pharmacological interventions for motion sickness: Cardiovascular Effects", Aviation, Space and Environmental Medicine, Sep. 1987, pp. A270-A276.

Temple, et al., "Loratadine, an Antihistamine, Blocks Antigen-and Ionophore-Induced Leukotriene Release from Human Lung in Vitro", Prostaglandins, Apr. 1988, 35(4):549-554.

The United States Pharmacopeia, The United States Formulary, United States Pharmacopeial Convention, Inc., Rockville, MD. 1989, p. 1990.

Van Cauwenberge, "New Data on the Safety of Loratadine", Drug Invest., 1992, vol. 4, No. 4, pp. 283-291.

Wade, et al., Handbook of Pharmaceutical Excipients ($2^{nd}$ edition), American Pharmaceutical Association and Pharma Press, Royal Pharma. Society of G. Britain, 1994, pp. 257&259.

Wein, "Pharmacology of Incontinence", Urologic Clinics of North America, Aug. 1995, vol. 22, No. 3, pp. 557-577.

Wirth, et al., Mailland Reaction of Lactose and Fluoxeline Hydrochloride, a Secondary Amine, Journal of Pharmaceutical Sciences , Jan. 1998,vol. 87, No. 1, pp. 31-39.

Wood, "Antimotion Sickness and Antiemetic Drugs", Drugs, 1979, vol. 17, pp. 471-479.

Wood, et al., "Mechanisms of Antimotion Sickness Drugs", Aviation, Space, and Environmental Medicine, Sep. 1987, pp. A262-A265.

Yarker, et al., "Oxybutynin,. A Review of its Pharmacodynamic and Phamacokinetic Properties, and its Therapeutic Use in Detrusor Instability", Drugs and Aging, 1995, vol. 6, No. 3, pp. 243-262.

Zhong, et al., "HPLC-Determination of Loratadine and its active metabolite descarboethoxyloratadine in human plasma", Pharmazie, 1994, vol. 49(H. 10), pp. 736-739.

* cited by examiner

CHART
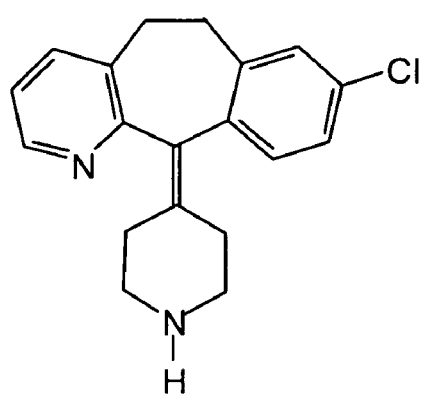
I
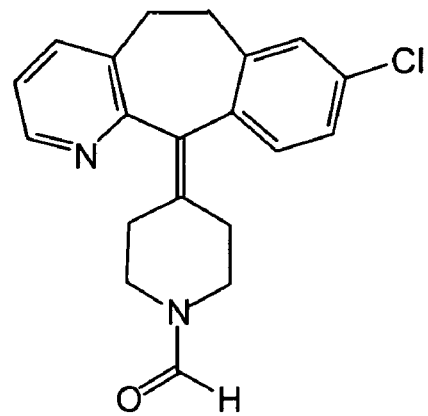
II
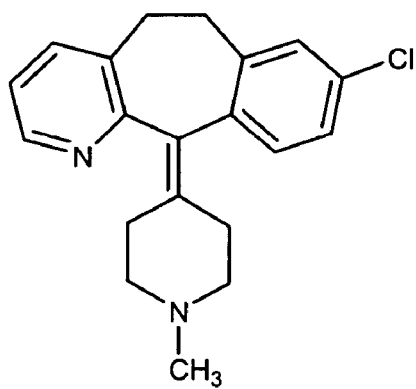
III

STABLE EXTENDED RELEASE ORAL DOSAGE COMPOSITION

CROSS-REFERENCE TO RELATED APPLICATIONS

This application is a continuation application of U.S. application Ser. No. 10/175,460 filed Jun. 19, 2002, now granted as U.S. Pat. No. 6,979,463 on Dec. 27, 2005, which is a continuation-in-part of PCT/US00/34412 filed Dec. 19, 2000, from which priority is claimed pursuant to 35 U.S.C. §365(c) and §120, which application claims priority to U.S. Provisional Application Ser. No. 60/172,836, filed Dec. 20, 1999 under 35 U.S.C. §119(e).

BACKGROUND

This invention relates to a film-coated extended release solid oral dosage composition containing a nasal decongestant, e.g., pseudoephedrine in a controlled release core and a film outer coating containing the non-sedating antihistamine, desloratadine. The solid oral dosage compositions of this invention are useful for treating patients showing the signs and symptoms associated with allergic and/or inflammatory conditions such as the common cold, as well as signs and symptoms associated with allergic and/or inflammatory conditions of the skin or upper and lower airway passages such as allergic rhinitis, seasonal allergic rhinitis and nasal congestion, upper respiratory diseases, allergic rhinitis and nasal congestion.

Desloratadine, also called descarboethoxyloratadine, is disclosed in U.S. Pat. No. 4,659,716 as a non-sedating antihistamine useful as an anti-allergy agent. U.S. Pat. No. 6,100,274 discloses compositions containing desloratadine. U.S. Pat. No. 5,595,997 discloses methods and compositions for treating seasonal allergic rhinitis symptoms using desloratadine. Desloratadine, upon oral absorption, is hydroxylated at the 3 position to produce the metabolite, 3-hydroxyldesloratadine.

U.S. Pat. Nos. 4,990,535 and 5,100,675 disclose a twice-a-day sustained release coated tablet wherein the tablet coating comprises descarboethoxyloratadine and a hydrophilic polymer and polyethylene glycol, and the tablet core comprises acetaminophen, pseudoephedrine or a salt thereof, a swellable hydrophilic polymer and pharmaceutically acceptable excipients.

U.S. Pat. No. 5,314,697 discloses an extended release tablet containing matrix core comprising pseudoephedrine sulfate and a coating comprising loratadine.

None of the prior art discloses the once-a-day film-coated solid oral dosage composition of this invention.

The successful development of a formulation of a desloratadine-pseudoephedrine once-a-day product would be desirable, but would require achieving a release rate profile for pseudoephedrine component over an extended period in excess of twelve hours and preferably at least 16 hours while maintaining delivery of an effective once a day dose of desloratadine.

It would be desirable for increased patient compliance to have an extended release desloratadine-pseudoephedrine product effective and safe when used on a once-a-day basis for the treatment, management and/or mitigation of the signs and symptoms associated with the common cold, as well as allergic and/or inflammatory conditions of the skin or upper and lower airway passages such as seasonal, allergic rhinitis and nasal congestion.

SUMMARY OF THE INVENTION

We have discovered a desloratadine-pseudoephedrine once-a-day product which produces a release rate profile for pseudoephedrine over an extended period in excess of twelve hours and preferably at least 16 hours while maintaining delivery of an effective once a day dose of desloratadine.

Thus, the present invention provides film-coated extended release solid oral dosage composition comprising (a) a core comprising an effective amount of pseudoephedrine or pharmaceutically acceptable salt thereof, and (b) a film coating uniformly covering the core and comprising an effective amount of desloratadine wherein the amount of pseudoephedrine or pharmaceutically acceptable salt thereof is effective to produce a geometric maximum plasma concentration of pseudoephedrine of about 345 ng/mL to about 365 ng/mL at a time of about 7.60 hrs to about 8.40 hrs and the amount of desloratadine is effective to produce a geometric maximum plasma concentration of desloratadine of about 2.10 ng/mL to about 2.45 ng/mL at a time of about 4.0 hours to about 4.5 hours after administration of a single dose of said composition.

Preferred embodiments of the film-coated extended release solid oral dosage composition of the present invention also produce a geometric maximum plasma concentration of 3-hydroxydesloratadine of about 0.75 ng/mL to about 1.15 ng/mL at a time of about 5.50 hours to about 6.25 hours after administration of a single dose of said composition.

More preferred embodiments of the film-coated extended release solid oral dosage composition of the present invention also produce a geometric maximum plasma concentration of desloratadine of about 2.10 ng/mL to about 2.45 ng/mL at a time of about 4.0 hours to about 4.5 hours and a geometric maximum plasma concentration of 3-hydroxydesloratadine of about 0.75 ng/mL to about 1.15 ng/mL at a time of about 5.50 hours to about 6.25 hours after administration of a single dose of said composition.

Thus, in a preferred embodiment, this invention provides a pharmaceutical composition comprising therapeutically effective amount of pseudoephedrine sulfate in a core and an effective amount of desloratadine in a film coating maintaining the desirable pharmacokinetic parameters of desloratadine, 3-hydroxydesloratadine and pseudoephedrine listed herein above and containing less than about 2% of desloratadine decomposition products such as N-formyldesloratadine, preferably less than about 1.4% to about 1.6% of the desloratadine decomposition products such as N-formyldesloratadine, initially, as well as when such compositions are stored at 25° C. and about 60% relative humidity for periods of at least about 24 months.

We have also discovered that by placing a first coating between film-coating comprising desloratadine and the core comprising a nasal decongestant, e.g., pseudoephedrine salt, preferably pseudoephedrine sulfate, provides release of desloratadine from the second film-coating and extended release of the nasal decongestant pseudoephedrine sulfate from the core, preferably a matrix core, over a period in excess of twelve hours while maintaining the desirable pharmacokinetic parameters of desloratadine, 3-hydroxydesloratadine and pseudoephedrine listed herein above and producing less than 2% degradation of the desloratadine to N-formyldesloratadine.

Thus, in a preferred embodiment, the present invention provides a film-coated extended release solid oral dosage composition comprising:

(a). a matrix core comprising:
1. an extended release amount of a pharmaceutically acceptable decongestant;
2. a polymer matrix;
3. a water insoluble basic calcium, magnesium or aluminum salt;
4. a binder;
5. a lubricant; and optionally,
6. a glidant;
(b) a first film coating uniformly covering the matrix core comprising;
1. a water-swellable film-forming neutral or cationic copolymeric ester;
2. a lubricant;
3. a film-modifier; and
4. optionally, an anti-foaming agent;
(c) a second film coating uniformly covering the first coating, comprising:
1. an immediate release amount of desloratadine;
2. a water-swellable film-forming neutral or cationic copolymeric ester;
3. a lubricant;
4. a water soluble film-modifier; and optionally,
5. an anti-foaming agent;

This preferred embodiment of the film-coated extended release solid oral dosage composition of the present invention releases at least about 80% of the desloratadine into a 0.1 N HCl solution at 37° C. within about 45 minutes and about 64% of the pseudoephedrine sulfate in 6 hours and 88% of the pseudoephedrine sulfate in 12 hours in a USP Paddle Method at 100 rpm wherein the film-coated extended release oral dosage composition contains less than about 2% of the desloratadine decomposition products such as N-formyldesloratadine.

In another preferred embodiment, the present invention provides a film-coated extended release solid oral dosage composition comprising:
(a) a matrix core comprising:

| Ingredient | mg/core |
| --- | --- |
| Pseudoephedrine Sulfate | about 240 |
| Hydroxypropyl Methylcellulose 2208 100,000 cps. | about 160-480 |
| Ethylcellulose | about 40-120 |
| Dibasic Calcium Phosphate Dihydrate | about 56-162 |
| Povidone | about 20-60 |
| Silicon Dioxide | about 6-12 |
| Magnesium Stearate | about 2-6 |
| Approximate Matrix Core Weigh Range: | about 518-1082 mg | and
(b) a first film coating uniformly covering the matrix core comprising:
(1) a neutral copolymer of ethyl acrylate and methyl acrylate;
(2) a lubricant selected from talc, silicon dioxide and magnesium stearate;
(3) a polyethylene glycol selected form polyethylene glycol 200 to polyethylene glycol 8000; and
(4) optionally, a pharmaceutically acceptable mixture of homologous liquid methyl siloxane polymers and silica gel; and
(c) a second film coating uniformly coating the first coating, comprising:
(1) an amount of desloratadine effective to produce a geometric maximum plasma concentration of desloratadine of about 2.10 ng/mL to about 2.45 ng/mL at a time of about 4.0 hours to about 4.5 hours after administration of a single dose of said composition;
(2) a neutral copolymer of ethyl acrylate and methyl acrylate;
(3) a lubricant selected from talc, silicon dioxide and magnesium stearate;
(4) a polyethylene glycol selected from polyethylene glycol 200 to polyethylene glycol 8000; and optionally
(5) a pharmaceutically acceptable mixture of homologous liquid methyl siloxane polymers and silica gel.

The above-listed preferred film-coated extended solid oral dosage composition may further comprise a third film coating uniformly covering the second film coating, wherein the third film coating comprises:
(1) a neutral copolymer of ethyl acrylate and methyl acrylate;
(2) a lubricant selected from talc, silicon dioxide and magnesium stearate;
(3) an effective amount of at least one a water-soluble film-modifying agent selected from low viscosity hydroxypropyl cellulose, methyl hydroxyethyl cellulose and sodium carboxymethyl cellulose, and a polyethylene glycol selected from polyethylene glycol 200 to polyethylene glycol 8000 or mixtures thereof;
(4) a pharmaceutically acceptable dye; and
(5) optionally a pharmaceutically acceptable mixture of homologous liquid methyl siloxane polymers and silica gel.

In a more preferred embodiment, the present invention provides a film-coated extended release solid oral dosage composition comprising:
(a) a matrix core comprising:

| Ingredient | mg/core |
| --- | --- |
| Pseudoephedrine Sulfate | about 240 |
| Hydroxypropyl Methylcellulose 2208 100,000 cps. | about 160-480 |
| Ethylcellulose | about 40-120 |
| Dibasic Calcium Phosphate Dihydrate | about 54-162 |
| Povidone | about 20-60 |
| Silicon Dioxide | about 6-12 |
| Magnesium Stearate | about 2-6 |
| Approximate (Matrix Core) Weight Range: | about 518-1082 mg |

(b) a first film coating uniform by covering the matrix core comprising:

| Ingredient | mg/first coating |
| --- | --- |
| (d) a neutral copolymer of ethyl acrylate and methyl acrylate having an average molecular weight of 800,000; | about 1.36-about 4.08 |
| (2) a lubricant selected from talc, silicon dioxide and magnesium stearate; | about 1.36-about 4.08 |
| (3) a polyethylene glycol selected from a polyethylene glycol 6000 to a polyethylene glycol 8000 and | about 0.136-about 0.408 |
| (4) optionally, a pharmaceutically acceptable mixture of homologous liquid methyl siloxane polymers and silica gel; | about 0.11-about 0.33 |
| Total for first film coating: | about 2.96-8.89 mg | and
(c) a second film coating uniformly coating the first coating, said second film comprising:

| Ingredient | mg/second film coating |
|---|---|
| (1) a 24-hour amount of desloratadine; | about 5.0-about 6.0 |
| (2) a neutral copolymer of ethyl acrylate and methyl acrylate having an average molecular weight of 800,000; | about 3.04-about 9.12 |
| (3) a lubricant selected from talc, silicon dioxide and magnesium stearate; | about 3.5-about 10.5 |
| (4) a polyethylene glycol selected from a polyethylene glycol 6000 to a polyethylene glycol 8000; and | about 0.915-about 2.75 |
| (5) optionally, a pharmaceutically acceptable mixture of homologous liquid methyl silsoxane polymers and silica gel; | about 0.14-about 042 |
| Total for second coating: | about 12.60-about 38.79 mg |

In a preferred embodiment, the present invention provides a film-coated extended release oral dosage composition comprising:
a. a matrix core comprising:

| Ingredient | mg/core |
|---|---|
| Pseudoephedrine Sulfate | about 240 |
| Hydroxypropyl Methylcellulose 2208 100,000 cps. | about 160-480 |
| Ethylcellulose | about 40-120 |
| Dibasic Calcium Phosphate | about 56-162 |
| Povidone | about 20-60 |
| Silicon Dioxide; and | about 6-12 |
| Magnesium Stearate | about 2-6 |
| Approximate Matrix Core Weight Range: | about 518-1082 mg |

(b) a first film coating uniform by covering the matrix core comprising:
(1) a neutral copolymer of ethyl acrylate and methyl acrylate having molecular weight of 800,000;
(2) a lubricant selected from talc, silicon dioxide and magnesium stearate;
(3) a polyethylene glycol selected from a polyethylene glycol 200 to polyethylene glycol 8000; and
(4) optionally a pharmaceutically acceptable mixture of homologous liquid methyl siloxane polymers and silica gel; and
(c) a second film coating uniformly covering the first coating comprising:
(1) an amount of desloratadine effective to produce a geometric maximum plasma concentration of desloratadine of about 2.10 ng/mL to about 2.45 ng/mL at a time of about 4.0 hours to about 4.5 hours after administration of a single dose of said composition;
(2) a neutral copolymer of ethyl acrylate and methyl acrylate having an average molecular weight of 800,000;
(3) a lubricant selected from talc, silicon dioxide and magnesium stearate;
(4) a polyethylene glycol selected from a polyethylene glycol 200 to a-polyethylene 8000; and
(5) optionally a pharmaceutically acceptable mixture of homogous liquid methyl siloxane and polymers and silica gel.

A more preferred composition of the present invention is provided herein below:

| 1. Matrix Core | |
|---|---|
| Ingredient | mg/core |
| Pseudoephedrine Sulfate USP | 240 |
| Hydroxypropyl Methylcellulose 2208 USP 100,000 cps | 320 |
| Ethylcellulose NF Type 7 | 80 |
| Dibasic Calcium Phosphate USP Dihydrate | 108 |
| Povidone USP | 40 |
| Silicon Dioxide NF | 8 |
| Magnesium Stearate NF | 4 |
| Approximate Matrix Core Weight: | 800 mg |

| 1. Matrix Core Coatings | |
|---|---|
| | mg/tablet |
| 1. First Film Coating: Ingredient | |
| Simethicone | 0.22 |
| Polyethylene glycol 8000 | 0.27 |
| Talc NF | 2.72 |
| Ethyl Acrytalc/Methyl Methacrylate neutral copolymer (30% dispersion in water) | 2.72 |
| Subtotal for first coating | 5.93 mg |
| Second Film(Immediate(Release)Coating | |
| Desloratadine | 6.0 |
| Simethicone | 0.28 |
| Polyethylene glycol 8000 | 1.83 |
| Talc NF | 5.88 |
| Ethyl Acrylate/Methyl methacrylate neutral copolymer | 6.09 |
| Subtotal for second coating | 20.08 mg |
| 3. Third Film Coating | |
| Hydroxypropyl Methylcellulose 2910 USP 6 cps | 2.09 |
| Talc NF | 5.79 |
| Ethyl Acrylate/Methyl Methacrylate Neutral copolymer | 4.18 |
| Polyethylene Glycol 8000 NF | 0.42 |
| Simethicone | 0.11 |
| Spectra Spray Med Blue Dye | 3.65 |
| Subtotal for third coating: | 16.24 mg |
| Approximate Total of Three Coatings Weight: | 42.37 mg |
| Approximate Tablet (MatrixCore and Three Coatings) Weight: | 842.97 mg |

Another more preferred composition of the present invention is provided herein below:

| Ingredient | mg/core |
|---|---|
| 1. Matrix Core | |
| Pseudoephedrine Sulfate USP | 240 |
| Hydroxypropyl Methylcellulose 2208 USP 100,000 cps | 320 |
| Ethylcellulose NF Type 7 | 80 |
| Dibasic Calcium Phosphate USP Dihydrate | 108 |
| Povidone USP | 40 |
| Silicon Dioxide NF | 8 |
| Magnesium Stearate NF | 4 |
| Approximate Matrix Core Weight: | 800 mg |

-continued

2. Matrix Core Coatings

| | mg/tablet |
|---|---|
| 1. First Film Coating: Ingredient | |
| Simethicone | 0.22 |
| Polyethylene glycol 8000 | 0.27 |
| Talc NF | 2.72 |
| Ethyl Acrytalc/Methyl Methacrylate neutral copolymer (30% dispersion in water) | 2.72 |
| Subtotal for first coating: | 5.93 mg |
| Second Film(Immediate Release)Coating | |
| Desloratadine | 5.0 |
| Simethicone | 0.28 |
| Polyethylene glycol 8000 | 0.61 |
| Talc NF | 5.17 |
| Ethyl Acrylate/Methyl methacrylate neutral copolymer | 6.09 |
| Hydroxypropyl Methylcellulose 2910 USP 6 cps | 3.05 |
| Subtotal for second coating: | 20.20 mg |
| 3. Third Film Coating | |
| Hydroxypropyl Methylcellulose 2910 USP 6 cps | 2.09 |
| Talc NF | 5.79 |
| Ethyl Acrylate/Methyl Methacrylate Neutral copolymer | 4.18 |
| Polyethylene Glycol 8000 NF | 0.42 |
| Simethicone | 0.11 |
| Spectra Spray Med Blue Dye | 3.65 |
| Subtotal for third coating | 16.24 mg |
| Approximate Total of Three Coatings Weight: | 42.37 mg |
| Approximate Tablet (MatrixCore & Three Coatings) Weight: | 842.37 mg |

Similar results would be expected if a decongestant effective amount of another pharmaceutically acceptable pseudoephedrine salt, e.g., pseudo-ephedrine hydrogen chloride was used in place of pseudoephedrine sulfate.

The compositions of the present invention are useful for treatment of allergic and/or inflammatory conditions of the skin (e.g. urticaria) and the upper and lower airway passages including the nasal and non-nasal symptoms of seasonal allergic rhinitis including nasal congestion in patients in need of such treating.

DETAILED DESCRIPTION OF THE DRAWINGS

Chart item I illustrates the chemical structure for desloratadine.

Chart item II illustrates the chemical structure for N-methyl-desloratadine.

Chart item III illustrates the chemical structure for N-formyldesloratadine.

DETAILED DESCRIPTION OF THE INVENTION

During the course of development of the compositions of the present invention, desloratadine was found to be unstable and to discolor when stored in combination with various excipients such as those disclosed in U.S. Pat. No. 5,314,697 as part of the matrix core containing pseudoephedrine sulfate. The excipients causing discoloration and instability of desloratadine include acidic excipients having a pH of less than 7 in water such as organic acids, such as stearic acid, povidone, crospovidone and carbonyl-containing materials such as lactose, and ethyl cellulose and hydroxylpropyl methylcellulose. Binders like povidone and polymers such as hydroxypropylmethylcellulose are useful as a polymer matrix for the sustained release of the pseudoephedrine sulfate from the inner polymer matrix core.

We discovered that by uniformly covering the inner core matrix containing a nasal decongestant, e.g., pseudoephedrine sulfate and hydroxypropyl methylcellulose, ethyl cellulose and povidone with a first coating comprising a water-swellable film-forming neutral or cationic copolymeric ester, a film modifier and lubricant, the desloratadine could safely be coated onto the first coating. The desloratadine was found to have an acceptable immediate release profile from the second coating (80% release in 0.1N HCl in less than about 45 min) and contain less than about 2% of N-formyldesloratadine, preferably about 1.4% to about 1.6% of N-formyldesloratadine even after storage for at least 24 months—preferably up to 36 months at 25° C. and about 60% relative humidity ("RH").

When a third film coating comprising a water swellable film-forming neutral or cationic co-polymeric ester and polyethylene glycol as a film modifier was placed on top of the second coating, the dissolution rate of desloratadine from the second coating and pseudoephedrine from the core decreased to unacceptably low levels.

Surprisingly, addition of a low viscosity hydroxylpropyl methylcellulose to the third coating as a film-modifier, restored the dissolution rates of both active ingredients (pseudoephedrine sulfate and desloratadine) to levels approximately the same as those obtained when a core matrix was uniformly covered with two film coatings.

The phrase "allergic and inflammatory conditions of the skin and airway passages" is meant those allergic and inflammatory conditions and symptoms found on the skin and in the upper and lower airway passages from the nose to the lungs. Typical allergic and inflammatory conditions of the skin and upper and lower airway passages include seasonal and perennial allergic rhinitis, non-allergic rhinitis, asthma including allergic and non-allergic asthma, sinusitis, colds (in combination with a NSAID, e.g., aspirin, ibuprofen or acetaminophen) and/or a decongestant e.g. pseudoephedrine), dermatitis, especially allergic and atopic dermatitis, and urticaria and symptomatic dermographism as well as retinopathy, and small vessel diseases, associated with diabetes mellitus.

The amount of desloratadine effective for treating or preventing allergic and inflammatory conditions of the skin and upper and lower airway passages will vary with the age, sex, body weight and severity of the allergic and inflammatory condition of the patient. Typically, the amount of desloratadine effective for treating or preventing such allergic and inflammatory conditions is in the range of about 2.5 mg/day to about 60 mg/day, preferably about 2.5 mg/day to about 20 mg/day, or about 4.0 mg/day to about 15 mg/day, or about 5.0 mg/day to about 10 mg/day, more preferably about 5.0 mg/day to about 10.0 mg/day, and most preferably about 5.0 mg/day to about 6.0 mg/day in a single dose.

Desloratadine is a non-sedating long acting histamine antagonist with potent selective peripheral H1-receptor antagonist activity. Following oral administration, loratadine is rapidly metabolized to descarboethoxyloratadine or desloratadine, a pharmacologically active metabolite. In vitro and in vivo animal pharmacology studies have been conducted to assess various pharmacodynamic effects of desloratadine and loratadine. In assessing antihistamine activity in mice (comparison of $ED_{50}$ value), desloratadine was relatively free of producing alterations in behavior alterations in behavior, neurologic or autonomic function. The potential for desloratadine or loratadine to occupy brain H1-receptors was assessed in guinea pigs following i.p. administration and results suggest poor access to central histamine receptors for desloratadine or loratadine.

In addition to antihistaminic activity, desloratadine has demonstrated anti-allergic and anti-inflammatory activity from numerous in vitro and in vivo tests. These in vitro tests (mainly conducted on cells of human origin) have shown that desloratadine can inhibit many events in the cascade of allergic inflammation. These anti-inflammatory effects for desloratadine are independent of the H1-antagonist effect of desloratadine and include: The release of inflammatory mediators histamine, truptase, leukotriene and prostaglandin D2 from mast cells;

The release of inflammatory cytokines including IL-4, IL-6, IL-8 and IL-13; The release of the inflammatory chemokines such as RANTES (regulated upon activation, normal T cell expressed and presumably secreted); Superoxide anion production of polymorphonuclear neutrophils; The expression of cell adhesion molecules such as intracellular adhesion molecules (ICAM-1) and P-selection in endothelial cells; and Eosinophil migration and adhesion In vivo studies also suggest that an inhibitory effect of desloratadine on allergic bronchospasm and cough can also be expected.

The clinical efficacy and safety of desloratadine has been documented in over 3,200 seasonal allergic rhinitis patients in 4 double-blind, randomized clinical trials The results of these chemical studies demonstrated the efficacy of desloratadine in the treatment of adult and adolescent patients with seasonal rhinitis.

The nasal decongestants useful in the present invention include phenylpropanolamine, phenylephrine and pseudoephedrine. Pseudoephedrine as well as pharmaceutically acceptable acid additional salts, e.g., those of HCl or $H_2SO_4$, is a sympathomimetic drug recognized by those skilled in the art as a safe therapeutic agent effective for treating nasal congestion and is commonly administered orally and concomitantly with an antihistamine for treatment of nasal congestion associated with allergic rhinitis. The use of pseudoephedrine as a nasal decongestant in the present invention is preferred; the use of pseudoephedrine sulfate is more preferred.

In the course of development of the oral dosage composition of this invention, it was discovered that the selection of the polymers for the polymer matrix core was critical to achieve the desired extended release period of at least 12 hours, preferably 12 to 16 hours and more preferably for at least 16 hours for pseudoephedrine sulfate. For example, the use of hydroxypropyl methyl cellulose 4,000 cps or 15,000 cps as polymers in the matrix core did not provide this more preferred extended release period of at least 16 hours for dose of pseudoephedrine sulfate. We discovered that only by selecting for inclusion into the matrix core of specific weight ratios of three specific polymers was the desired pseudoephedrine release profile achieved. Only by combining (1) four parts by weight of hydroxypropyl methyl cellulose 2208 USP, 100,000 cps with (2) one part by weight of ethyl cellulose together with (3) 1/2 part by weight of povidone as a secondary binder was the more preferred extended release profile of at least 16 hours for pseudoephedrine sulfate from the matrix core achieved. The matrix core also contains specific amounts of silicon dioxide as a glidant and magnesium stearate as a lubricant. The tablet hardness 22±6 Strong-Cobb Units (SCU) is not greatly affected by the higher level of lubricant (6 mg/tablet) but it is preferred to maintain the lubricant level at 1/10 part by weight of lubricant to one part by weight of povidone as secondary binder.

The term "lubricant" as used herein refers to a substance added to the dosage form to enable the dosage form, e.g., a tablet, after it has been compressed to releases from the mold or die.

Suitable lubricants include talc, magnesium stearate, calcium stearate, stearic acid, hydrogenated vegetable oils and the like. Preferably, magnesium stearate or talc is used.

The term "glidants" as used herein refers to a substance, such as an anti-caking agent, which improves the flow characteristics of a powder mixture.

Suitable glidants include silicon dioxide and talc. Preferably, silicon dioxide is used.

The term "binders" as used herein means any material that is added to pharmaceutical compositions to help hold such compositions together and release the medicament therefrom.

Suitable binders are selected from the group consisting of: croscarmellose sodium, a cross-linked polymer of carboxymethylcellulose sodium, povidone, crospovidone, starches, celluloses, alginates, and gums; see also USP XXII page 1858 (1990). Preferably, povidone is used.

Typically suitable antifoaming agents include mixtures of homologous liquid methylsiloxane and silica gel available under the Simethecone tradename.

The term "water-swellable film-forming neutral or cationic copolymeric ester," as used herein means neutral and cationic copolymers of ethyl acrylate and substituted unsubstituted methyl or ethyl methacrylate esters.

Typically suitable water swellable film-forming neutral copolymeric esters include neutral copolymers of ethyl acrylate and methyl methacrylate such as are available from Pharma Polymers, a company of the Hüls Group under the EUDRAGIT® Tradename; EUDRAGIT NE30D. and Kollicoat available from BASF, Mt Olive, N.J. An aqueous dispersion containing 30% by weight of a neutral copolymer based on ethyl acrylate and methyl methacrylate (average molecular weight of approximately 800,000) is preferred.

Typically suitable water-swellable film-forming cationic co-polymeric esters include cationic co-polymers based on dimethylaminoethylmethacrylate and a neutral methacrylic ester such as the EUDRAGIT E copolymers available from Pharma Polymers as a 12.5% solution (EUDRAGIT E 12.5) or as solid (EUDRAGIT E 100) and quaternary ammonium copolymers described in USP/NF as "Amononio methacrylate copolymer, Type A" and Type "B". Such copolymers are available as aqueous dispersions of copolymers of acrylic and methacrylic acid esters with a low (substitution) content of quaternary ammonium groups present as salts, (e.g., quaternary ammonium chlorides). Type A and Type B are available as 30% aqueous dispersions under the EUDRAGIT RL 30D and EUDRAGIT RS 30D tradenames, respectively. Use of the water-swellable film-from neutral co-polymeric esters based on ethyl acrylate and methacrylate is preferred.

The term "water soluble film modifier" as used herein means a film-forming agent which modifies the water-swellable characteristics of the film-forming neutral or cationic copolymeric esters useful in the compositions of the present invention. A typically suitable water soluble film-modifying agent is a low viscosity ($\leq 20$ cps) cellulose such as low viscosity hydroxypropyl methyl cellulose, low viscosity hydroxylethyl methyl cellulose; low viscosity sodium carboxymethyl cellulose or a polyethylene glycol selected from polyethylene glycol 200 to polyethylene glycol 8000.

Use of a polyethylene glycol 6000 to polyethylene glycol 8000 as a film modifier is preferred in the first and second coatings; the use of polyethylene glycol 8000 in each coating is more preferred.

Use of polyethylene glycol in combination with a low viscosity hydroxypropyl methylcellulose in the third coating is preferred. Use of a mixture of polyethylene glycol 8000 and hydroxypropyl methylcellulose 2910 cps in the third or outermost film coating is more preferred.

The term "water insoluble basic calcium, magnesium and aluminium salts" as used herein means the pharmaceutically acceptable carbonates, phosphates, silicates and sulfates of calcium, magnesium and aluminum or mixtures thereof. Typically suitable pharmaceutically acceptable basic salts include calcium sulfate anhydrous, hydrates of calcium sulfate, such as calcium sulfate dihydrate, magnesium sulfate anhydrous, hydrates of magnesium sulfate, dibasic calcium phosphate, dibasic calcium silicate, magnesium trisilicate, magnesium phosphate, aluminum silicate, and hydrates of magnesium phosphate, aluminum phosphate; and calcium phosphate is more preferred. The use of dibasic calcium phosphate dihydrate is most preferred.

The hydroxylpropyl methylcellulose 2910 acts as a film-forming agent in the film coating, and the polyethylene glycols act as film modifier. Other suitable film-forming polymers which may be used include low viscosity (720 cps) hydroxypropyl celluloses, methyl hydroxyethyl cellulose and sodium carboxymethyl cellulose.

The oral dosage composition of this invention also provides a shelf life of more than 24 months, e.g., up to 36 and 48 months so long as the tablets are stored in standard package at between 20 and 30° C. in an ambient environment of 60% relative humidity.

In the preparation of the tablet core, the povidone is dissolved in a mixture of alcohol and water. The pseudoephedrine sulfate, hydroxypropyl methylcellulose 2208 USP, 100,000 cps, ethylcellulose, and dibasic calcium phosphate are blended and granulated with an alcoholic water solution containing povidone. The granulation is milled, and dried to a loss on drying between 0.5 to 2.0%.

The dried granulation is milled and blended with requisite amounts of silicon dioxide and magnesium stearate. The final blend is compressed to produce the inner polymer matrix core composition.

The coatings are normally applied to the inner polymer matrix cores in the following manner:

Cores are charged into a suitable coating pan. A water dispersion of talc, Simethicone, polyethylene glycol 8000 and EUDRAGIT NE30D is applied to the matrix cores as a first coating. These coated matrix cores are then coated with a dispersion of desloratadine, Simethicone, EUDRAGIT NE30D, polyethylene glycol 8000 NF and talc dispersion. This is followed by an application of third coating containing a dispersion of FD & C Blue No. 2 Aluminum lake containing EDTA as a chelating agent, talc, Simethicone, EUDRAGIT NE30D, containing hydroxy-propyl methylcellulose 2910 cps. and polyethylene glycol 8000 NF. The coated tablets are then branded (with black ink) and packaged in plastic bottles and blisters for storage at a temperature between 2° C. and 30° C. in an ambient environment.

During the course of development of the formulations of the present invention, we discovered that the in vitro dissolution studies showed a decrease in both the desloratadine release rate and in desloratadine concentration at increased pH, especially pH values >7.0, compared to those for a 5 mg tablet of desloratadine. The in vivo studies showed the Tmax was greater than 4 hours and that a significant part of the absorptive desloratadine process occurs in the small intestine which has an alkaline pH (pH values >7.0).

We discovered we could increase the release of desloratadine by increasing the level of hydroxypropyl methylcellulose and lowering the levels of the plasticizing agent, e.g., polyethylene glycol 8000, and of the lubricant, e.g., talc, in the second film coating containing desloratadine. See Example 4.

In another preferred embodiment, the effective amount of desloratadine in the second film coating was increased to 6.0 mg and amount of talc was reduced (by about 1.12 mg) to produce an acceptable pharmacokinetic profile. See Example 3 and Table 3.

For the solid oral dosage formulations of the present invention, the geometric mean maximum plasma concentration of pseudoephedrine (PES) is about 345 ng/mL to about 365 ng/mL at a time (Tmax) of about 7.60 hours to about 8.40 hours; the geometric mean maximum plasma concentrate of desloratadine (DL) is about 2.10 ng/mL to about 2.45 ng/mL, preferably 2.15 ng/mL to about 2.35 ng/mL at a time (Tmax), of about 4.0 hours to about 4.5 hours and the geometric mean maximum plasma concentrate of 3-hydroxydesloratadine (3-OH-DL) is about 0.75 ng/mL to about 1.15 ng/mL, preferably about 0.85 ng/mL to about 1.05 ng/mL, and more preferably preferably about 0.88 ng/mL to about 1.02 ng/mL at a time (Tmax) of about 5.50 hours to about 6.25 hours after administration of a single dose of said composition to healthy subjects.

Pharmacokinetic Study No. 1

The pharmacokinetic objective of this study was to determine the bioavailability and bioequivalence of desloratadine (DL), 3-OH DL and pseudoephedrine (PES) from the formulation of Example 2 (5 mg of DL/240 mg of PES) of this application relative to that of a 5 mg of Example 11 of U.S. Pat. No. 6,100,274 (U.S. Pat. No. '274) and an extended-release pseudoephedrine core as references. This study was a Phase I, open-label, single-dose, randomized, three-way crossover study with a seven-day washout period between each treatment. Thirty-six healthy male and female subjects received each of the following treatments in the order assigned by a computer-generated random code:

| | |
|---|---|
| Treatment A: | One 5 mg DL/240 mg PES tablet of Example 2. |
| Treatment B: | One DL 5 mg tablet of Example 11 of USP.'274. |
| Treatment C: | One 240 mg pseudoephedrine sulphate (oval extended-release pseudoephedrine cores from Claritin ® D-24 coated with placebo Claritin ® D-24 coat). |

The tablets were administered with 180 mL (6 fluid ounces) of non-carbonated room temperature water. The tablet was swallowed whole, not chewed or crushed. After dosing, the oral cavity was inspected to assure that the subject had swallowed the tablet. Subjects continued fasting until the four-hour study procedures were complete. Water was permitted throughout the fasting period, except for two hours post-dose. The subjects remained awake and seated upright/ambulatory for four hours post-dose. All subjects were confined to the study site until the 120-hour blood samples, vital signs and laboratory tests were obtained.

Serial blood samples (10 mL) were to be collected into tubes containing heparin as an anticoagulant at the following time points: 0 (pre-dose), 0.5, 1, 1.5, 2, 3, 4, 5, 6, 8, 10, 12, 16, 20, 24, 36, 48, 48, 72, 96 and 120 hours post-dose. No food was allowed for four hours after dosing. Drinking water was not allowed from one hour pre-dose to one hour postdose, except for the 120 mL administered with the treatment. Plasma concentrations of pseudoephedrine were determined using a validated liquid chromatography with tandem mass spectrometric (LC/MS/MS) method with a lower limit of quantitation (LOQ) of 10.0 ng/mL, and a linear range of 10.0-400 ng/mL. The associated mean pharmacokinetic parameters are provided in Table 1.

The mean DL Cmax following administration of DL tablet of Example 2 of the present invention or a 5 mg desloratadine tablet of Example 11 of U.S. Pat. No. 6,100,274 were 1.79 and 2.23 ng/mL, respectively, and were reached at mean Tmax values of 6.78 and 5.10 hours, respectively.

TABLE 1

Mean (% CV[a]) Pharmacokinetic Parameters of DL, and 3-OH DL in Healthy Subjects Following Single-Dose Oral Administration of DL D-24 and DL

| | DL | | | |
|---|---|---|---|---|
| | Example 2-5 mg/240 mg (Treatment | | Example 11 of USP'274-5 mg (Treatment B | |
| Parameter (units) | Mean | % CV | Mean | % CV |
| Cmax(ng/mL) | 1.79 | 35.8 | 2.23 | 34.8 |
| Tmax(hr) | 6.78 | 57.3 | 5.10 | 52.5 |
| | 3-OH DL | | | |
| | Example 2-D-24 5 mg/240 mg (Treatment | | Example 11 of USP'274-5 mg (Treatment B) | |
| | Mean | % CV | Mean | % CV |
| Cmax(ng/mL) | 0.695 | 59.4 | 0.832 | 55.2 |
| Tmax(hr) | 6.09[b] | 32.7 | 4.96[b] | 31.4 |

[a]% CV is percent coefficient of variation, which is a relative measure of variability. See Steele and Torrie, "Principles and Procedures of Statistics", (1980) 2nd Edition, McGraw-Hill, NY, at page 27.
[b]n = 35

The mean 3-OH DL Cmax following administration of 5 mgDL/240 mgPES tablet of Example 2 of this application and a 5 mg desloratadine tablet of Example 11 of U.S. Pat. No. 6,100,274 were 0.695 and 0.832 ng/mL, respectively, and were reached at mean Tmax values of 6.09 and 4.96 hours, respectively. The peak plasma concentration of 3-OH DL decreased slowly with half-life of 29.6 hours following administration of 5 mgDL/240 mgPES tablet of Example 2 of this application, and 29.5 hours following administration of the 5 mg DL tablet of U.S. Pat. No. 6,100,274.

Statistical comparisons of Cmax and AUC(tf) following administration of tablet of Example 2 of this application and 5 mg desloratadine tablet of U.S. Pat. No. 6,100,274 were performed for DK and 3-OH DL plasma concentrations.

The results showed that the 90% confidence intervals for DL and 3-OH DL did not meet the 80-125% bioequivalence guidelines for both Cmax and AUC(tf). For those subjects where AUC(I) could be determined, the confidence intervals of DL for AUC(I) did not meet the 80-125 bioequivancy guidelines. However, the confidence intervals of 3-OH DL for AUC(I) did meet the 80-125 bioequivances guidelines.

The mean pharmacokinetic parameters of pseudoephedrine are provided in Table 2.

TABLE 2

Mean (% CV[a]) Pharmacokinetic Parameters of Pseudoephedrine in Healthy Subjects Following Single-Dose Oral Administration of DL D-24 and 240 mg Pseudoephedrine Sulphate (Oval Extended-Release Pseudoephedrine Cores from Claritin ® D-24 Coated with Placebo Claritin ® D-24 Coat) Tablets (n = 36)

| | Pseudoephedrine | | | |
|---|---|---|---|---|
| | Example 2 of this application 5 mg/240 mg | | Pseudoephedrine Sulphate (Oval-Extended Release Pseudoephedrine Cores from Claritin D-24) | |
| | Mean | % CV | Mean | % CV |
| Cmax(ng/mL) | 328 | 25 | 349 | 18.1 |
| Tmax(hr) | 8.42 | 34 | 7.36 | 36.3 |
| AUC(tf)(ng-hr/mL) | 6438 | 42 | 6225 | 38.5 |
| tf(hr) | 44.0 | 37 | 40.0 | 25.8 |
| AUC(I)(ng-hr/mL) | 6780 | 40 | 6452 | 37.3 |
| t½(hr) | 10.3 | 148 | 7.25 | 21.6 |

[a]% CV is percent coefficient of variation, which is a relative measure of variability. See Steele and Torrie, "Principles and Procedures of Statistics", (1980) 2nd Edition, McGraw-Hill, NY, at page 27.

The mean pseudoephedrine Cmax following administration of the (5 mg DL/240 mgPES) tablet of Example 2 or a 240 mg pseudoephedrine sulphate extended-release core were 328 and 349 ng/mL, respectively. Statistical comparisons of Cmax and AUC(tf) values for DL D-24 (5 mg/240 mg) versus 240 mg pseudoephedrine sulphate (extended-release core) were performed. The power to detect a 20% difference in treatment means at an α-level of 0.05 (two-tailed) for the log-transformed Cmax and AUC(tf) were 100 and 93%, respectively.

The 90% confidence intervals for pseudoephedrine met the 80-125% bioequivalence guidelines for both Cmax and AUC (tf). For those subjects were AUC(I) could be determined, the confidence intervals for AUC(I) also met the 80-125 guidelines.

Pharmacokinetic Study No. 2

Subjects were confined at the study site at least 12 hours prior to each treatment (Day-1). In the morning of Day 1, following a ten-hour overnight fast, each subject received one of the following treatments based on his/her subject number and the study period:

Treatment A: One (5 mg DL/240 mgPES) tablet of Example 2 of this application

Treatment B: One (6 mgDL/240 mgPES) tablet of Example 3 of this application

Treatment C: One 5 mg DL tablet of Example 11 of U.S. Pat. No. '274 plus one 120 mg PES tablet (oval extended-release pseudoephedrine core)

The study procedures, blood collection times and the analytical methodologies summarized in Study No. 1 were employed.

The mean pharmacokinetic parameters are shown in Table 3. The power to detect a 20% difference in treatment means of DL at an α-level of 0.05 (two tailed) for the log-transformed AUC(tf), AUC(I), and Cmax values were 89%, 90% and 88% respectively.

TABLE 3

Mean (% CV[1]) Pharmacokinetic Parameters of DL,
3-OH DL and Pseudoephedrine in Healthy Adult Volunteers
(n = 42) Following Single-Dose Oral Administration of
DI Tablets of Examples 2 (5 mg DL/240 mgPES), Example 3
(6 mg DL/240 mg PES) or a 5 mg DL Tablet of USP'274
Plus One 240 mg PES Tablet.

| | DL | | | |
|---|---|---|---|---|
| Treatment | Cmax(ng/mL)/ | CV | Tmax(hr)/ | CV |
| A[2] | 1.91 | 44 | 4.69 | 52 |
| B[3] | 2.35 | 43 | 4.33 | 50 |
| C[4] | 2.28 | 40 | 3.87 | 67 |

| | 3-OH DL | | | |
|---|---|---|---|---|
| Treatment | Cmax(ng/mL)/ | CV | Tmax(hr)/ | CV |
| A[2] | 0.77 | 28 | 6.67 | 52 |
| B[3] | 1.00 | 39 | 6.12 | 48 |
| C[4] | 0.93 | 31 | 5.68 | 58 |

| | Pseudoephedrine | | | |
|---|---|---|---|---|
| Treatment | Cmax(ng/mL) | CV | Tmax(hr)/ | CV |
| A[2] | 353 | 30 | 7.71 | 45 |
| B[3] | 362 | 28 | 8.14 | 46 |
| C[4] | 349 | 22 | 8.31 | 47 |

[1]% CV is percent coefficient of variation, which is a relative measure of variability. See Steele and Torrie, "Principles and Procedures of Statistics", (1980) 2$^{nd}$ Edition, McGraw-Hill, NY, at page 27.
[2]Treatment A = One (5 mg/240 mg) tablet of Example 2.
[3]Treatment B = One (6 mg/240 mg) tablet of Example 3.
[4]Treatment C = One 5 mg DL tablet of Example II of U.S. Pat. No. 6,100,274 plus one 240 mg pseudoephedrine tablet.

The results show that, based on plasma 3-OH DL concentrations, the (5 mg/240 mg) of Example 2 is not equivalent to the 5 mg DL tablet of Example 11 of U.S. Pat. No. '274 and that the 6 mgDL/240 PESmg of Example 3 and 5 mg DL tablet of Example II of U.S. Pat. No. '274 are bioequivalent.

The results show that, the bioequivalence of pseudoephedrine from the formulations of Examples 2 & 3 was established relative to the reference product.

Pharmacokinetic Study No. 3

Forty health volunteers were enrolled in this open label, randomized, three-way cross-over, single-dose study. The subjects were randomized to receive, following a ten hour over-night fast:

| Treatment A: | 5 mg DL/240 mg PES of Example 4 of this appln |
| Treatment B: | DL 5 mg of Example11 of USP '274 Plus 240 mg PES |

The procedures of Study No. 1 were followed using the above-listed treatments.

The mean pharmacokinetic parameters for DL, 3-OH DL and pseudoephedrine are provided in Table 4.

TABLE 4

Mean (% CV[1]) Pharmacokinetic Parameters of DL, 3-OH DL and
Pseudoephedrine in Healthy Adult Volunteers (n = 40) Following
Single-Dose Oral Administration of One 5 mg D-24 Tablet of Example
4 or One 5 mg DL Tablet of USP'274 Plus One 240 mg
Pseudoephedrine Sulfate Tablet

| | DL | | | |
|---|---|---|---|---|
| Treatment | Cmax(ng/mL)/CV | | Tmax(hr)/CV | |
| A[2] | 2.15 | 41 | 4.13 | 66 |
| B[3] | 2.30 | 44 | 4.83 | 62 |

| | 3-OH DL | |
|---|---|---|
| Treatment | Cmax(ng/mL) | Tmax(hr) |
| A[2] | 0.89 | 48 | 5.60 | 42 |
| B[2] | 1.07 | 36 | 6.10 | 37 |

| | Pseudoephedrine | |
|---|---|---|
| Treatment | Cmax(ng/mL) | Tmax(hr) |
| A[2] | 382 | 34 | 7.83 | 29 |
| B[2] | 399 | 32 | 8.43 | 36 |

[1]% CV is percent coefficient of variation, which is a relative measure of variability. See Steele and Torrie, "Principles and Procedures of Statistics", (1980) 2$^{nd}$ Edition, McGraw-Hill, NY, at page 27.
[2]Treatment A = One (5 mgDL/240 mgPES) tablet of Example 4 of this application.
[3]Treatment B = One 5 mg DL tablet of Example 11 of U.S. Pat. No. 6,100,274 plus one 240 mg pseudoephedrine tablet.

EXAMPLE 1

This example illustrates preparation of the preferred oral dosage composition of this invention. The ingredients and specific amounts thereof are listed below.

1. Matrix Core
   A. Method of Manufacture:
   1. Dissolve povidone in a mixture of 3 parts of alcohol and 1 part of purified water.
   2. Combine the pseudoephedrine sulfate, hydroxypropyl methylcellulose 2208, ethylcellulose and dibasic calcium phosphate, dihydrate in a suitable mixing bowl and blend under a nitrogen overlay.
   3. Granulate the blend from Step 2 with the solution from Step. 1. pass the wet granulation through suitable milling equipment to breakup large lumps.
   4. Dry the wet granulation at about 70° C. in a suitable fluid bed processor to a loss on drying between 0.5 to 2.0% as determined by a moisture balance or equivalent.
   5. Pass the dried granules through suitable milling equipment.
   6. Add the requisite amounts of silicon dioxide and magnesium stearate to the dried, milled granules and blend.
   7. Compress the blend on a suitable tablet press.

The matrix cores are coated in the following manners:
A. Preparation of Coating Dispersions and Solutions
1. First Film Coating Solution
   (1) Disperse Simethicone and polyethylene glycol 8000 in a portion of purified water and agitate until completely dissolved.
   (2) To the product of step 1, add the remainder of the purified water and the talc; stir the so-formed suspension at room temperature until homogeneous.
   (3) Slowly add the so-formed homogeneous suspension of step 2 to the stirred EUDRAGIT NE30D dispersion and continue to mix the so-formed mixture until a homogeneous dispersion is formed. Pass the dispersion through a screen.

(4) Spray the dispersion onto the matrix cores maintained at 40° C.±5° C. on a rotating pan.

(5) Dry the cooled matrix cores on the rotating pan.

2. Second Film Coating Dispersion (1) Disperse the Simethicone and polyethylene glycol 8000 in a portion of purified water. Add additional water and stir the dispersion at room temperature until completely dissolved.

(2) Slowly add desloratadine to the dispersion of step 1 and mix until a uniform dispersion is formed. Combine with the talc with the so-formed uniform dispersion, and continue agitation until a homogenous suspension is formed.

(3) Add dispersion of step 2 to the EUDRAGIT NE 30D dispersion and mix until a uniform dispersion is formed. Pass the dispersion through a screen.

(4) Spray the requisite amount of the dispersion from step 3 onto the matrix core with the first coating in a rotating pan at 25-27° C.

(5) Dry the coated matrix cores on the rotating pan.

3. The Third Film Coating Solution (1) Add the hydroxypropyl methylcellulose 2910 to hot purified water (75° C.) and agitate until a solution forms. Cool the so-formed solution to room temperature.

(2) To a separate container, add Simethicone and polyethylene glycol 8000 to purified water and continue to mix until a solution is formed.

(3) Add talc to solution of step 2 and continue to mix until a uniform dispersion is formed.

(4) Add the solution of step 1 to the dispersion of step 3 and continue to mix until (5) Add FD&C Blue No. 2 aluminum lake containing EDTA as a chelating agent to purified water in a third container and (6) Add the Blue lake solution of step 5 to the dispersion of step 4 and mix until a homogeneous mixture is formed.

(7) Slowly add the mixture of step 6 to a dispersion of EUDRAGIT NE30D and continue to mix until homogeneous.

(8) Pass dispersion of step 6 through 60 mesh screen.

(9) Spray the requisite amount of the dispersion of step 8 onto the twice-coated matrix cores in a rotating pan at 35°-45° C. Dry the thrice-coated matrix cores in the form of tablets in rotating pan.

(10) Remove the so-formed tablets from pan and further dry at 40° for 16 hours.

| -continued |  |
|---|---|
| Povidone USP | 40 |
| Silicon Dioxide NF | 8 |
| Magnesium Stearate NF | 4 |
| Approximate Matrix Core Weight: | 800 mg |

3. Matrix Core Coatings

| | mg/tablet |
|---|---|
| 1. First Film Coating: Ingredient | |
| Simethicone | 0.22 |
| Polyethylene glycol 8000 | 0.27 |
| Talc NF | 2.72 |
| Ethyl Acrytalc/Methyl Methacrylate neutral copolymer (30% dispersion in water) | 2.72 |
| Subtotal for first coating | 5.93 mg |
| 2. Second Film(Immediate Release)Coating | |
| Desloratadine | 5.0 |
| Simethicone | 0.28 |
| Polyethylene glycol 8000 | 1.83 |
| Talc NF | 7.00 |
| Ethyl Acrylate/Methyl methacrylate neutral copolymer | 6.09 |
| Subtotal for second coating | 20.20 mg |
| 3. Third Film Coating | |
| Hydroxypropyl Methylcellulose 2910 USP 6 cps | 2.09 |
| Talc NF | 5.79 |
| Ethyl Acrylate/Methyl Methacrylate Neutral copolymer | 4.18 |
| Polyethylene Glycol 8000 NF | 0.42 |
| Simethicone | 0.11 |
| Spectra Spray Med Blue Dye | 3.65 |
| Subtotal for third coating: | 16.24 mg |
| Approximate Total of Three Coatings Weight: | 42.37 mg |

Approximate Tablet (MatrixCore & Three Coatings) Weight: 842.97 mg

The in vitro dissolution profile of the tablet of Example 1 was measured in a stirred 0.1N HCl solution at 37° C. (1st hour) and thereafter in a stirred phosphate buffer having a pH of 7.5 at 37° C. The 80% of desloratadine in the coating was dissolved within the first 45 minutes and the total dose of pseudoephedrine sulfate in the matrix core was slowly released via erosion and dissolution mechanisms over a period of at least 16 hours.

EXAMPLE 2

The following more preferred composition of the present invention was made in accordance with the above procedure of Example 1.

1. Matrix Core

| Ingredient | mg/core |
|---|---|
| Pseudoephedrine Sulfate USP | 240 |
| Hydroxypropyl Methylcellulose 2208 USP 100,000 cps | 320 |
| Ethylcellulose NF Type 7 | 80 |
| Dibasic Calcium Phosphate USP Dihydrate | 108 |

EXAMPLE 3

The following more preferred composition of the present invention was made in accordance with the above procedure of Example 1.

1. Matrix Core

| Ingredient | mg/core |
|---|---|
| Pseudoephedrine Sulfate USP | 240 |
| Hydroxypropyl Methylcellulose 2208 USP 100,000 cps | 320 |
| Ethylcellulose NF Type 7 | 80 |
| Dibasic Calcium Phosphate USP Dihydrate | 108 |

-continued

| | |
|---|---|
| Povidone USP | 40 |
| Silicon Dioxide NF | 8 |
| Magnesium Stearate NF | 4 |
| Approximate Matrix Core Weight: | 800 mg |

4. Matrix Core Coatings

| | mg/tablet |
|---|---|
| 1. First Film Coating:<br>Ingredient | |
| Simethicone | 0.22 |
| Polyethylene glycol 8000 | 0.27 |
| Talc NF | 2.72 |
| Ethyl Acrytalc/Methyl Methacrylate neutral copolymer (30% dispersion in water) | 2.72 |
| Subtotal for first coating | 5.93 mg |
| Second Film(Immediate Release)Coating | |
| Desloratadine | 6.0 |
| Simethicone | 0.28 |
| Polyethylene glycol 8000 | 1.83 |
| Talc NF | 5.88 |
| Ethyl Acrylate/Methyl methacrylate neutral copolymer | 6.09 |
| Subtotal for second coating | 20.08 mg |
| 3. Third Film Coating | |
| Hydroxypropyl Methylcellulose 2910 USP 6 cps | 2.09 |
| Talc NF | 5.79 |
| Ethyl Acrylate/Methyl Methacrylate Neutral copolymer | 4.18 |
| Polyethylene Glycol 8000 NF | 0.42 |
| Simethicone | 0.11 |
| Spectra Spray Med Blue Dye | 3.65 |
| Subtotal for third coating | 16.24 |
| Approximate Total of Three Coatings Weight: | 42.37 mg |
| Approximate Tablet (Matrix Core and Three Coatings) Weight: | 842.97 mg |

EXAMPLE 4

The following more preferred composition of the present invention was made in accordance with the above procedure of Example 1.

1. Matrix Core

| Ingredient | mg/core |
|---|---|
| Pseudoephedrine Sulfate USP | 240 |
| Hydroxypropyl Methylcellulose 2208 USP 100,000 cps | 320 |
| Ethylcellulose NF Type 7 | 80 |
| Dibasic Calcium Phosphate USP Dihydrate | 108 |
| Povidone USP | 40 |
| Silicon Dioxide NF | 8 |
| Magnesium Stearate NF | 4 |
| Approximate Matrix Core Weight: | 800 mg |

Matrix Core Coatings
5. Matrix Core Coatings

| | mg/tablet |
|---|---|
| 1. First Film Coating:<br>Ingredient | |
| Simethicone | 0.22 |
| Polyethylene glycol 8000 | 0.27 |
| Talc NF | 2.72 |
| Ethyl Acrytalc/Methyl Methacrylate neutral copolymer (30% dispersion in water) | 2.72 |
| Subtotal for first coating | 5.93 mg |
| Second Film(Immediate Release)Coating | |
| Desloratadine | 5.0 |
| Simethicone | 0.28 |
| Polyethylene glycol 8000 | 0.61 |
| Talc NF | 5.17 |
| Ethyl Acrylate/Methyl methacrylate neutral copolymer | 6.09 |
| Hydroxypropyl Methylcellulose 2910 USP 6 cps | 3.05 |
| Subtotal for second coating | 20.20 mg |
| 3. Third Film Coating | |
| Hydroxypropyl Methylcellulose 2910 USP 6 cps | 2.09 |
| Talc NF | 5.79 |
| Ethyl Acrylate/Methyl Methacrylate Neutral copolymer | 4.18 |
| Polyethylene Glycol 8000 NF | 0.42 |
| Simethicone | 0.11 |
| Spectra Spray Med Blue Dye | 3.65 |
| Subtotal for third coating | 16.24 mg |
| Approximate Total of Three Coatings Weight: | 42.37 mg |
| Approximate Tablet (Matrix Core and Three Coatings) Weight: | 842.37 mg |

Similar results would be expected if a decongestant effective amount of another pharmaceutically acceptable pseudoephedrine salt, e.g., pseudo-ephedrine hydrogen chloride was used in place of pseudoephedrine sulfate.

The compositions of the present invention are useful for treatment of allergic and/or inflammatory conditions of the skin (e.g. urticaria) and the upper and lower airway passages including the nasal and non-nasal symptoms of seasonal allergic rhinitis including nasal congestion in patients in need of such treating. The precise dosage and dosage regimen may be varied by the attending clinician in view of the teachings herein depending upon the requirements of the patient, e.g., the patient's age, sex and the severity of the allergic and/or inflammatory condition being treated. Determination of the proper dosage and dosage regimen for a particular patient will be within the skill of the attending clinician.

While we have hereinabove presented a number of preferred embodiments of this invention by way of example, it is apparent that the scope of the invention is to be defined by the scope of the appended claims.

What is claimed is:

1. A pharmaceutical tablet comprising: (a) a sustained release core comprising about 240 mg of pseudoephedrine or a pharmaceutically acceptable salt thereof; (b) a first film coating covering the core that is free from destabilizing amounts of stearic acid, povidone, crospovidone, lactose, ethyl cellulose and hydroxypropylmethyl cellulose 2208 and (c) a second film coating, comprising about 5 mg of desloratadine, covering the first coating, wherein the tablet is formulated to produce total desloratadine degradation products in the tablet of not more than 2.0% by weight after actual or simulated storage at about 25° C. and about 60% relative humidity for at least 24 months.

2. The pharmaceutical tablet of claim 1, formulated for once daily administration.

3. The pharmaceutical tablet of claim 1, further comprising hydroxypropylmethyl cellulose 2910 in a third film coating.

4. The pharmaceutical tablet of claim 1, further comprising polyethylene glycol.

5. The pharmaceutical tablet of claim 1, further comprising simethicone.

6. The pharmaceutical tablet of claim 1, further comprising talc.

7. The pharmaceutical tablet of claim 1, wherein at least 80% of the desloratadine in the tablet dissolves into a stirred 0.1N HCl solution at about 37° C. in less than 45 minutes.

8. The pharmaceutical tablet of claim 1, wherein at least 80% of the pseudoephedrine or pharmaceutically acceptable salt thereof in the tablet dissolves into a stirred 0.1N HCl solution at about 37° C. (1st hour) and thereafter in a stirred phosphate buffer having a pH of about 7.5 at about 37° C. in less than 16 hours.

9. The pharmaceutical tablet of claim 1, formulated to produce total desloratadine degradation products in the tablet of about 1.4% to about 1.6% by weight of N-formyldesloratadine, after actual or simulated storage at about 25° C. and about 60% relatively humidity for at least 24 months.

10. The pharmaceutical tablet of claim 1, wherein, after administration of a single dose of the tablet to a human, the mean time to maximum plasma concentration (Tmax) of desloratadine occurs at about 6-7 hours post dose.

11. The pharmaceutical tablet of claim 1, wherein administration of a single dose of the tablet to a human produces a peak plasma concentration (Cmax) of desloratadine of about 1.79 ng/mL.

12. The pharmaceutical tablet of claim 1, wherein, after administration of a single dose of the tablet to a human, the mean time to maximum plasma concentration (Tmax) of pseudoephedrine occurs at about 8-9 hours post dose.

13. The pharmaceutical tablet of claim 1, wherein administration of a single dose of the tablet to a human produces a peak plasma concentration (Cmax) of pseudoephedrine of about 328 ng/mL.

14. The pharmaceutical tablet of claim 1, wherein daily administration of the tablet to a human produces a mean steady state area under the concentration time curve (AUC(0-24 hrs)) of pseudoephedrine of about 6438 ng·hr/mL.

15. A pharmaceutical tablet comprising a sustained release core comprising about 240 mg of pseudoephedrine or a pharmaceutically acceptable salt thereof, and an immediate release coating comprising about 5 mg of desloratadine, wherein
    the tablet is formulated for once daily administration;
    the tablet comprises a water-swellable film-forming neutral or cationic copolymeric ester in a coating between the core and the immediate release coating; and
    the tablet is formulated to produce total desloratadine degradation products in the tablet of not more than 2.0% by weight, after actual or simulated storage at about 25° C. and about 60% relative humidity for at least 24 months.

16. The pharmaceutical tablet of claim 1, comprising polyethylene glycol, talc and simethicone.

* * * * *